(12) United States Patent
Li et al.

(10) Patent No.: US 10,085,484 B2
(45) Date of Patent: Oct. 2, 2018

(54) ATOMIZER AND REFILLABLE ELECTRONIC CIGARETTE HAVING SAME

(71) Applicant: Shenzhen First Union Technology Co., Ltd., Shenzhen, Guangdong Province (CN)

(72) Inventors: Yonghai Li, Shenzhen (CN); Zhongli Xu, Shenzhen (CN); Changzheng Dai, Shenzhen (CN); Xingbing Zou, Shenzhen (CN)

(73) Assignee: SHENZHEN FIRST UNION TECHNOLOGY CO., LTD., Shenzhen, Guangdong Province (CN)

(*) Notice: Subject to any disclaimer, the term of this patent is extended or adjusted under 35 U.S.C. 154(b) by 15 days.

(21) Appl. No.: 15/133,200

(22) Filed: Apr. 19, 2016

(65) Prior Publication Data

US 2016/0227841 A1   Aug. 11, 2016

(30) Foreign Application Priority Data

May 30, 2015   (CN) .................... 2015 2 0360577 U

(51) Int. Cl.
| | |
|---|---|
| A61M 15/06 | (2006.01) |
| A24F 47/00 | (2006.01) |
| A61M 16/20 | (2006.01) |
| B65B 3/10 | (2006.01) |
| B65D 47/00 | (2006.01) |
| H05B 3/42 | (2006.01) |

(52) U.S. Cl.
CPC ............ A24F 47/008 (2013.01); A61M 15/06 (2013.01); A61M 16/20 (2013.01); B65B 3/10 (2013.01); B65D 47/00 (2013.01); H05B 3/42 (2013.01); *H05B 2203/021* (2013.01)

(58) Field of Classification Search
CPC .. A61M 15/00; A61M 15/06; A61M 15/0001; A61M 15/0021; A61M 15/0033; A24F 47/008; A24F 47/002; A24F 47/004; H15B 2203/021
USPC ........ 131/329, 273, 223; 128/202.21, 200.14
See application file for complete search history.

(56) References Cited

U.S. PATENT DOCUMENTS

| | | | |
|---|---|---|---|
| 2015/0164146 A1* | 6/2015 | Li ......................... | A24F 47/008 131/329 |
| 2016/0286860 A1* | 10/2016 | Flayler ................. | A24F 47/008 |
| 2017/0065001 A1* | 3/2017 | Li .......................... | F16K 15/14 |

* cited by examiner

*Primary Examiner* — Vanessa Girardi
(74) *Attorney, Agent, or Firm* — Cheng-Ju Chiang

(57) ABSTRACT

An exemplary atomizer includes a housing, a receiving chamber defined in the housing, an atomizing unit arranged in the housing, and a deformable valve hermetically engaged in the liquid inlet. The receiving chamber is configured for storing tobacco liquid, and the receiving chamber has a liquid inlet. The atomizing unit is configured for generating aerosol from the tobacco liquid. The valve is capable of deforming upon an external force exerted by an injector, so that tobacco liquid can be injected into the receiving chamber via the liquid inlet, and capable of restoring to its original shape to seal the liquid inlet when the injector is moved out.

14 Claims, 6 Drawing Sheets

ATOMIZER AND REFILLABLE ELECTRONIC CIGARETTE HAVING SAME

TECHNICAL FIELD

The present invention relates to electronic cigarettes, and particularly to a refillable atomizer and an electronic cigarette using same.

BACKGROUND ART

A typical refillable atomizer includes a liquid chamber with a liquid inlet. The liquid inlet is usually sealed by an end piece. To inject tobacco liquid, the end piece is first opened.

However, when a user of the refillable atomizer injects tobacco liquid into the refillable atomizer, the refillable atomizer may be over turned due to carelessness. In this case, the tobacco liquid may leak from atomizer, thus rendering unsatisfactory.

What are needed, therefore, are an atomizer and an electronic cigarette using same, which can overcome the above shortcomings.

SUMMARY

An atomizer includes a housing, a receiving chamber defined in the housing, an atomizing unit arranged in the housing, and a deformable valve hermetically engaged in the liquid inlet. The receiving chamber is configured for storing tobacco liquid, and the receiving chamber has a liquid inlet. The atomizing unit is configured for generating aerosol from the tobacco liquid. The valve is capable of deforming upon an external force exerted by an injector, so that tobacco liquid can be injected into the receiving chamber via the liquid inlet, and capable of restoring to its original shape to seal the liquid inlet when the injector is moved out.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

DETAILED DESCRIPTION

Figure 1:
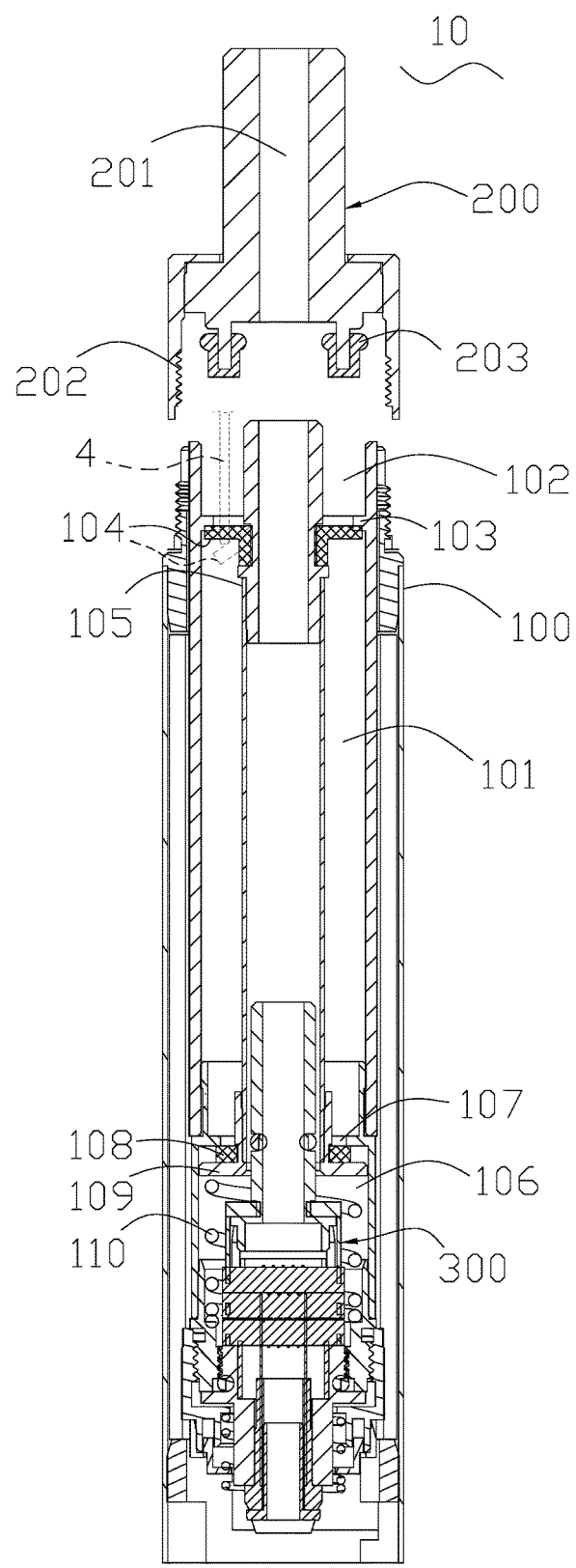
FIG. 1 is a cross-sectional view of an atomizer according to a first embodiment, including a mouthpiece and a housing, when the mouthpiece and housing are separated from each other.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Several definitions that apply throughout this disclosure will now be presented.

The term "outside" refers to a region that is beyond the outermost confines of a physical object. The term "inside" indicates that at least a portion of a region is partially contained within a boundary formed by the object. The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "comprising," when utilized, means "including, but not necessarily limited to"; it specifically indicates open-ended inclusion or membership in the so-described combination, group, series and the like.

Figure 2:
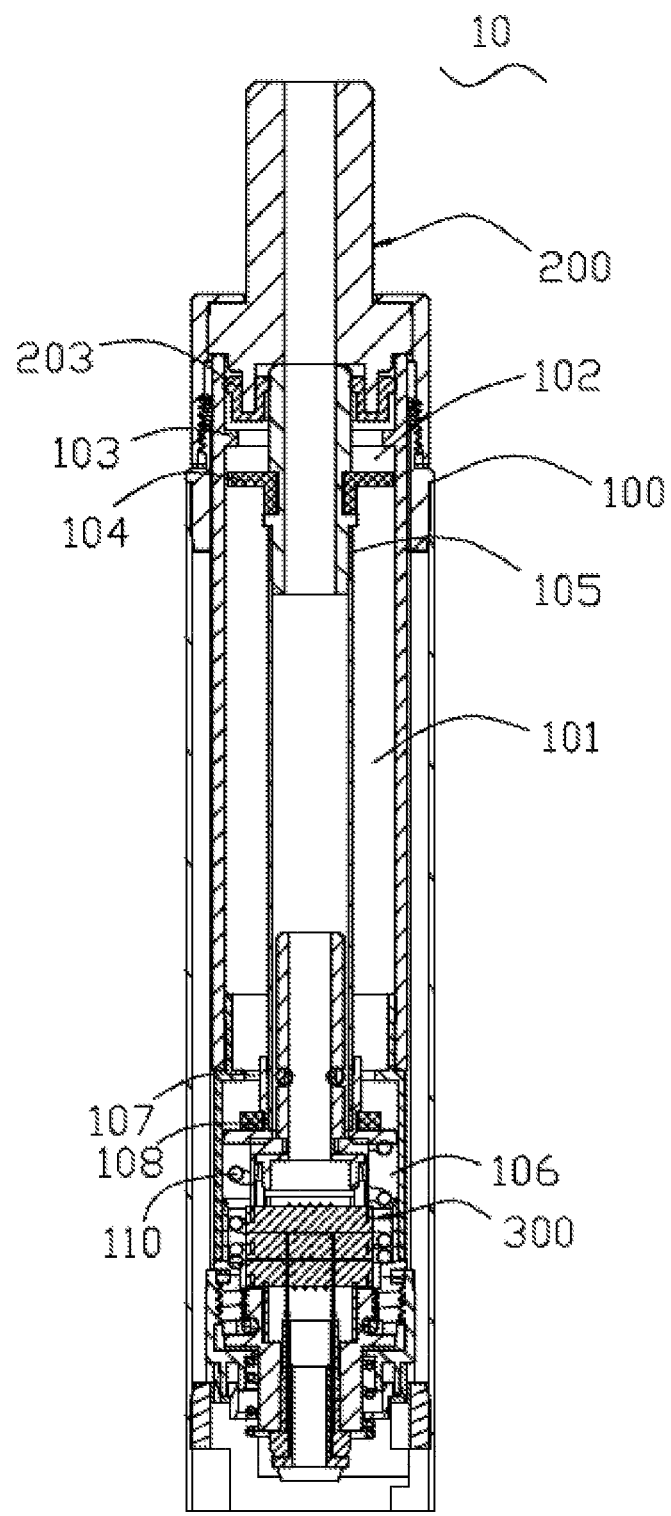
FIG. 2 is a cross-sectional view of the atomizer of FIG. 1 when assembled.

Referring to FIGS. 1-2, a refillable atomizer 10 includes a housing 100, an atomizing unit 300 in the housing 100, and a receiving chamber 101 defined in the housing 100. The receiving chamber 101 is configured (i.e., structured and arranged) for storing tobacco liquid filled by an external injector 4 (See FIG. 1, depicted via broken lines). The receiving chamber 101 includes a liquid inlet 102. The injector 4 usually includes a long and thin pinhead, and the pinhead may be plugged into the receiving chamber 101 via the liquid inlet 102. In this way, the tobacco liquid is injected into the receiving chamber 101. The atomizing unit 300 is adapted for generating aerosol from the tobacco liquid. The atomizer 10 further includes a resilient valve 104 sealing the liquid inlet 102. The valve 104 is pushed open by the injector 4 (Also see FIG. 1, the opened valve 104 is depicted via broken lines), so that the tobacco liquid is injected into the receiving chamber 101. When the injector 4 is moved away from the liquid inlet 102, the valve 104 restores to its original shape to seal the liquid inlet 102 again.

In the present embodiment, the receiving chamber 101 extends along an axial direction of the housing 100, and the valve 104 is positioned in the liquid inlet 102. The atomizing unit 300 is arranged in a bottom opening of the receiving chamber 101. The valve 104 is made of resilient material, for example, silica gel. If the atomizer 10 is overturned during injection, the injector 4 leaves from the liquid inlet 102, and the valve 104 restores to its original shape to seal the liquid inlet 102, thus avoiding liquid leakage from the liquid inlet 102.

The atomizer 10 further includes a mouthpiece 200 detachably connected with the housing 100. The mouthpiece 200 includes a sealing part 203 configured for sealing the liquid inlet 102. In the present embodiment, the mouthpiece 200 is fixedly connected to the housing 100 via screw threads, and the mouthpiece 200 includes a screw structure 202. When filling in tobacco liquid, the mouthpiece 200 should be detached first.

An air pipe 105 is further provided in the receiving chamber 101. One end of the air pipe 105 is connected to the atomizing unit 300, and the other end of the air pipe 105 is connected with the mouthpiece 200. The mouthpiece 200 defines an air outlet 201. The aerosol is inhaled via the air outlet 201. An elastic element 110 abuts against an end of the air pipe 105 connected with the atomizing unit 300. In the present embodiment, the elastic element 110 is a spring. The elastic element 110 is capable of driving a top end of the air pipe 105 to abut against the mouthpiece 200, and capable of driving the air pipe 105 to move upwards axially when the mouthpiece 200 is screwed off.

The atomizer 10 includes a liquid storing chamber 106 arranged under the receiving chamber 101. At least one liquid hole 107 communicates the liquid chamber 106 and the receiving chamber 101. A first seal ring 108 sleeves a bottom end of the air pipe 105. The first seal ring 108 is capable of moving together with the air pipe 105 to seal or open the liquid hole 107. A base 109 is provided at a bottom end of the air pipe 105, the first seal ring 108 is fixed on the base 109, and the elastic element 110 abuts against a bottom surface of the base 109. A top end of the atomizing unit 300 is hermetically connected with the air pipe 105, and is axially movable relative to the air pipe 105.

Figure 3:
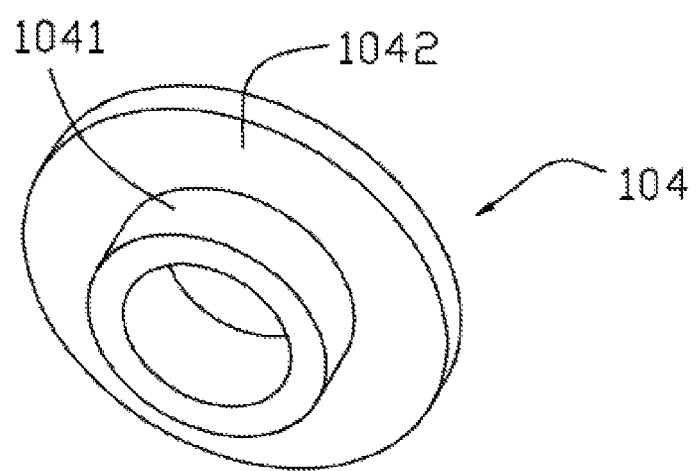
FIG. 3 is a perspective view of a valve in the atomizer of FIG. 1.

Referring to FIGS. 1 and 3, quite usefully, the valve 104 includes a casing main body 1041 and a deformable part 1042. The casing main body 1041 nests the air pipe 105. The deformable part 1042 extends outward from the air pipe 105. A step part 103 is provided in the liquid inlet 102, and the deformable part 1042 abuts against a bottom surface of the step part 103.

When the injector is plugged into the liquid inlet 102, the deformable part 1042 is deformed and pushed open. When the injector 4 is moved out, the deformable part 1042 restores to its original shape, and tightly abuts against the bottom surface of the step part 103, thus sealing the liquid inlet 102 again.

Referring to FIG. 1 again, when the mouthpiece 200 is screwed off, tobacco liquid can be filled in the atomizer 10, the air pipe 105 is driven to move up axially by the elastic element 110 until the first seal ring 108 seals the liquid hole 107. Accordingly, during liquid injection, the tobacco liquid cannot flow into the liquid storing chamber 106, thus avoiding liquid leakage.

Referring to FIG. 2 again, after the liquid injection is finished and the mouthpiece 200 is screwed on, the sealing part 203 seals the liquid inlet 102, and the mouthpiece 200 forces the air pipe 105 to move down axially. The first seal ring 108 is also driven to move downwards, and the liquid hole 107 is opened, so that the tobacco liquid in the receiving chamber 101 can flow into the liquid storing chamber 106. In this position, the atomizing unit 300 can absorb the tobacco liquid from the receiving chamber 101, and work normally. The valve 104 is also moved down with the air pipe 105.

Figure 4:
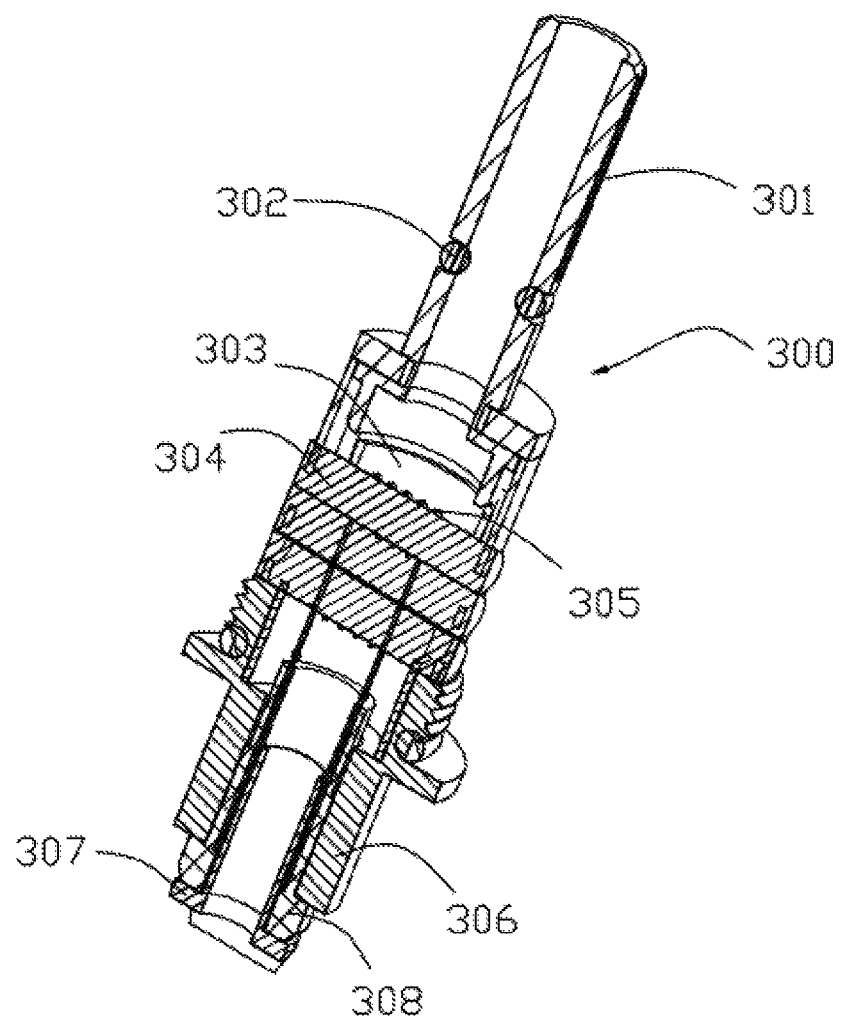
FIG. 4 is a partially cut-away view of an atomizing unit in the atomizer of FIG. 1.

Referring to FIG. 4, quite usefully, the atomizing unit 300 includes a main body 301, and the main body 301 defines an atomizing chamber 303. At least one liquid conducting body 304 and a heating element 305 are arranged in the atomizing chamber 303. The heating element 305 is in contact with the liquid conducting body 304. The liquid conducting body 304 is configured for conveying the tobacco liquid to the heating element 305. In the present embodiment, three liquid conducting bodies 304 are arranged in parallel in the atomizing chamber 303. The liquid conducting bodies 304 are made of porous material, e.g., glass fiber. The heating element 305 is a heating wire wound around one or more liquid conducting bodies 304. The heating wire 305 heats the tobacco liquid to form aerosol. A second seal ring 302 nests an upper end of the main body 301. The upper end of the main body 301 is inserted into the air pipe 105, and is hermetically connected with the air pipe 105 via the second seal ring 302. The upper end of the main body 301 is slidable relative to the air pipe 105.

The atomizing unit 300 is an independent component. When broken, the atomizing unit 300 may be replaced by a new one. A first contact electrode 306 and a second contact electrode 307 are arranged at a bottom end of the main body 301, and are insulated from each other by an insulated sleeve 308. The first contact electrode 306 and the second contact electrode 307 are electrically connected with two ends of the heating element 305, respectively. The first contact electrode 306 and the second contact electrode 307 are configured for connecting to two electrodes of a power supply 20 (see FIG. 5).

Figure 5:
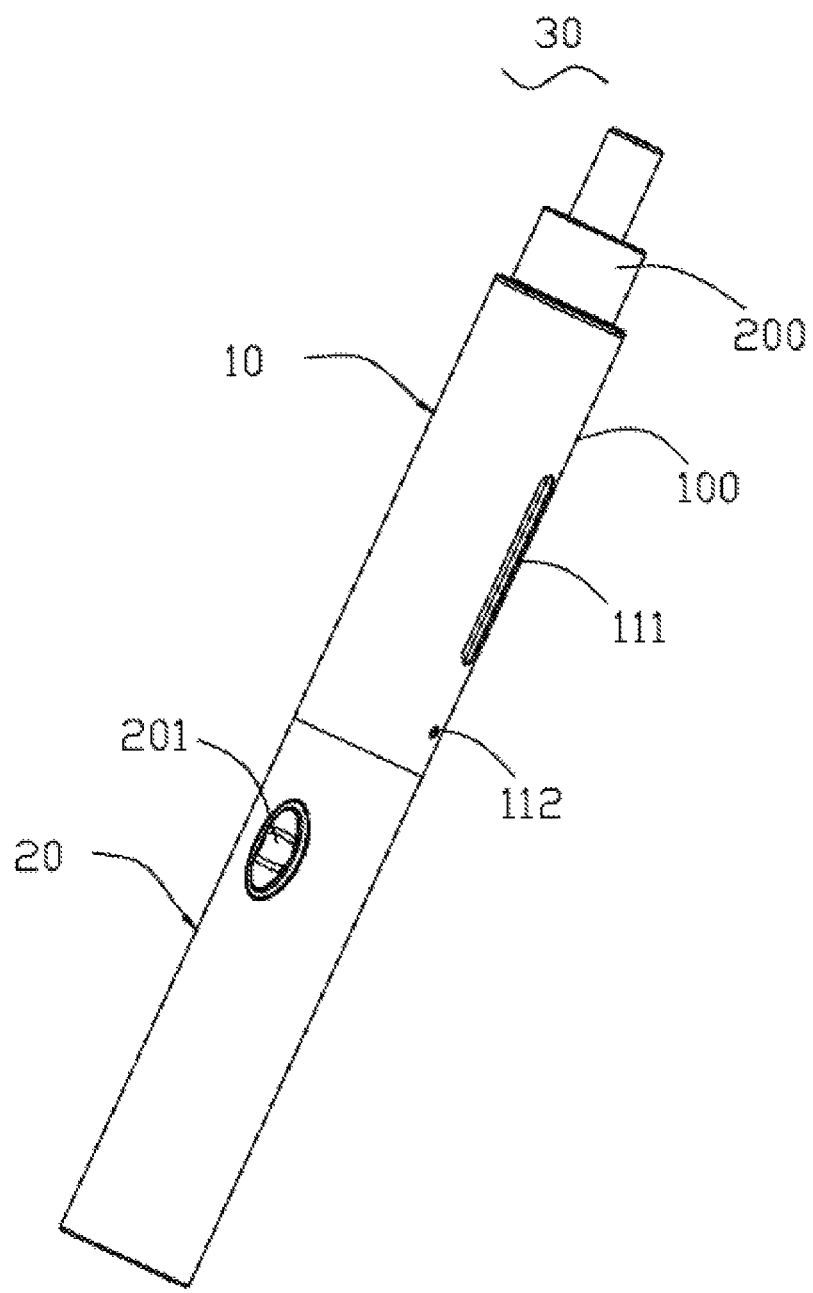
FIG. 5 is a perspective view of an electronic cigarette according to a second embodiment.

Referring to FIG. 5, an electronic cigarette 30 includes the above atomizer 10 and a power supply 20. The power supply 20 is detachably connected with the atomizer 10, and configured for feeding the atomizer 10 power. The housing 100 further defines an air inlet 112, and an observation window 111. A user of the electronic cigarette 30 can see an amount of the tobacco liquid through the observation window 111. A switch 201 is arranged in a housing of the power supply 20. When the switch 201 is pressed, the power supply 20 provides the atomizing unit 300 power (as seen in FIG. 1), and the electronic cigarette 30 starts working.

Figure 6:
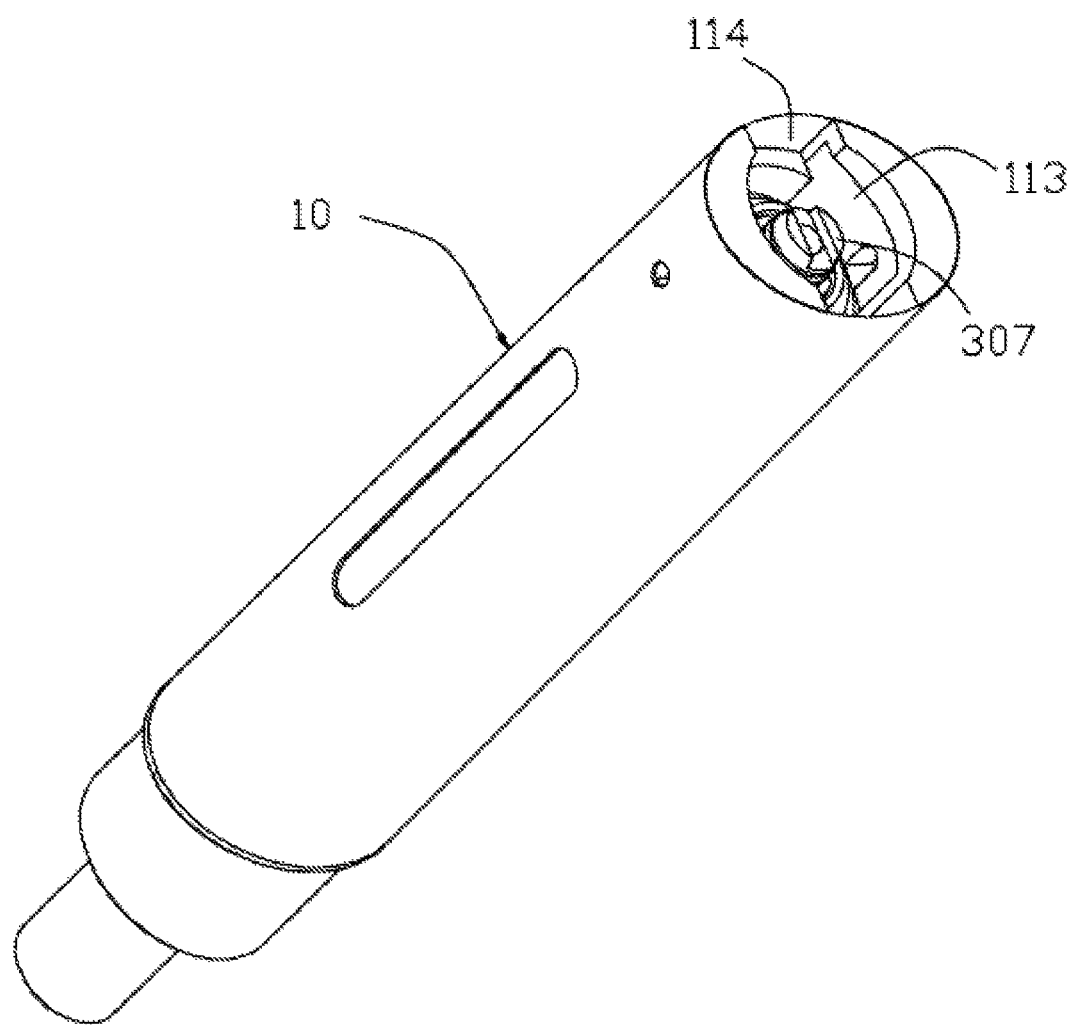
FIG. 6 is a perspective view of a perspective view of an atomizer in the electronic cigarette of FIG. 5.

Referring to FIG. 6, in the present embodiment, the atomizer 10 and the power supply 20 are coupled by rotation snap joint. The atomizer 10 includes a connection end defining a gap 114 and an arc-shaped groove 113. In assembly, the power supply 20 is inserted into the gap 114, and is then rotated a predetermined angle to engage in the arc-shaped groove 113. When the atomizer 10 is coupled with the power supply 20, positive and negative electrodes of the power supply 20 contacts with the first and the second contact electrodes 306 307, respectively.

It is understood that the above-described embodiments are intended to illustrate rather than limit the disclosure. Variations may be made to the embodiments and methods without departing from the spirit of the disclosure. Accordingly, it is appropriate that the appended claims be construed broadly and in a manner consistent with the scope of the disclosure.

What is claimed is:

1. An atomizer of a refillable electronic cigarette using an external injector for refill of tobacco liquid, comprising:
    a housing;
    a receiving chamber defined in the housing, the receiving chamber being configured for storing tobacco liquid, the receiving chamber having a liquid inlet;
    an atomizing unit arranged in the housing, the atomizing unit being configured for generating aerosol from the tobacco liquid; and
    a deformable valve hermetically engaged in the liquid inlet to seal the liquid inlet in an original position of the valve, a central portion of the valve being immovably fixed, and an edge portion of the valve other than the central portion being capable of deforming from the original position due to insertion of the external injector into the liquid inlet so that tobacco liquid is able to be refilled by the injector into the receiving chamber via the liquid inlet, and the valve being capable of restoring from deforming of the edge portion of the valve and back to the original position to seal the liquid inlet when the injector is moved out of the liquid inlet.

2. The atomizer according to claim 1, wherein the atomizing unit comprises a liquid conducting body and a heating element in contact with the liquid conducting body, and the liquid conducting body is configured for conveying the tobacco liquid to the heating element for atomization.

3. The atomizer according to claim 1, further comprising a mouthpiece detachably connected with an end of the housing adjacent to the liquid inlet, wherein the mouthpiece comprises a sealing part configured for sealing the liquid inlet.

4. The atomizer according to claim 3, further comprising an air pipe in the receiving chamber, wherein an end of the air pipe is connected to the atomizing unit, and an opposite end of the air pipe is in communication with the mouthpiece.

5. The atomizer according to claim 4, further comprising an elastic element, wherein the elastic element abuts against the end of the air pipe connected to the atomizing unit, the elastic element is configured for forcing the air pipe to abut against the mouthpiece, and driving the air pipe to move axially when the mouthpiece is screwed off.

6. The atomizer according to claim 5, further comprising a liquid storing chamber adjacent to the receiving chamber, wherein the atomizer defines a liquid hole communicating the receiving chamber and the liquid storing chamber, the atomizer further comprises a seal ring nesting the air pipe, and the seal ring is movable along an axial direction of the air pipe to open or close the liquid hole.

7. The atomizer according to claim 6, wherein the atomizing unit is arranged in the liquid storing chamber, and is configured for absorbing the tobacco liquid and generating aerosol from the tobacco liquid.

8. The atomizer according to claim 5, wherein the valve nests the air pipe, and is movable together with the air pipe.

9. The atomizer according to claim 8, wherein the valve comprises a casing main body nesting the air pipe and a deformable part extending outwards from the casing main body.

10. The atomizer according to claim 9, further comprising a step part in the liquid inlet, wherein the deformable part abuts against a bottom surface of the step part.

11. The atomizer according to claim 9, wherein the valve is made of silica gel.

12. An electronic cigarette refillable by an external injector, comprising:
an atomizer comprising:
a housing;
a receiving chamber defined in the housing, the receiving chamber being configured for storing tobacco liquid, the receiving chamber having a liquid inlet for insertion of the external injector into the liquid inlet to refill the tobacco liquid in the receiving chamber;
an atomizing unit arranged in the housing, the atomizing unit being configured for generating aerosol from the tobacco liquid; and
a deformable valve disposed in the liquid inlet and across the liquid inlet to hermetically engage in the liquid inlet for sealing the liquid inlet, the valve comprising a casing main body immovably disposed at a center of the valve and a deformable part extending from the casing main body outward to an edge of the valve to be deformable at the edge of the valve between a first position where the deformable part deforms at the edge of the valve toward an inside of the receiving chamber due to the insertion of the external injector, and a second position where the deformable part restores back to engage hermetically in the liquid inlet after removal of the external injector from the liquid inlet; and
a power supply detachably connected with the atomizer, the power supply being configured for supplying the atomizer power.

13. The electronic cigarette according to claim 12, wherein the atomizer and the power supply are coupled by rotation snap joint.

14. An atomizer of a refillable electronic cigarette using an external injector for refill of tobacco liquid, comprising:
a housing;
a receiving chamber defined in the housing, the receiving chamber being configured for storing tobacco liquid, the receiving chamber having a liquid inlet;
an atomizing unit arranged in the housing, the atomizing unit being configured for generating aerosol from the tobacco liquid;
a deformable valve hermetically engaged in the liquid inlet to seal the liquid inlet in an original position of the valve, the valve being capable of deforming from the original position due to insertion of the external injector into the liquid inlet so that tobacco liquid is able to be refilled by the injector into the receiving chamber via the liquid inlet, and the valve being capable of restoring from deforming of the valve and back to the original position to seal the liquid inlet when the injector is moved out of the liquid inlet;
a mouthpiece detachably connected with an end of the housing adjacent to the liquid inlet, wherein the mouthpiece comprises a sealing part configured for sealing the liquid inlet;
an air pipe in the receiving chamber, wherein an end of the air pipe is connected to the atomizing unit, and an opposite end of the air pipe is in communication with the mouthpiece; and
an elastic element, wherein the elastic element abuts against the end of the air pipe connected to the atomizing unit, the elastic element is configured for forcing the air pipe to abut against the mouthpiece, and driving the air pipe to move axially when the mouthpiece is screwed off.

* * * * *